United States Patent
Lu et al.

(10) Patent No.: US 9,968,524 B2
(45) Date of Patent: May 15, 2018

(54) CONTRAST PATTERN APPLICATION FOR THREE-DIMENSIONAL IMAGING

(71) Applicant: ARGES IMAGING, INC., Pasadena, CA (US)

(72) Inventors: Jian Lu, San Gabriel, CA (US); David Licata, Los Angeles, CA (US)

(73) Assignee: ARGES IMAGING, INC., Pasadena, CA (US)

( * ) Notice: Subject to any disclaimer, the term of this patent is extended or adjusted under 35 U.S.C. 154(b) by 0 days. days.

(21) Appl. No.: 15/388,558

(22) Filed: Dec. 22, 2016

(65) Prior Publication Data
US 2017/0105905 A1    Apr. 20, 2017

Related U.S. Application Data (60) Division of application No. 14/638,915, filed on Mar. 4, 2015, now Pat. No. 9,561,281, which is a continuation of application No. 13/424,200, filed on Mar. 19, 2012, now Pat. No. 8,999,371.

(51) Int. Cl.
| | |
|---|---|
| A61K 6/00 | (2006.01) |
| C09D 139/06 | (2006.01) |
| C09D 7/12 | (2006.01) |
| C09D 5/33 | (2006.01) |
| A61K 6/10 | (2006.01) |
| C09D 5/02 | (2006.01) |
| A61C 9/00 | (2006.01) |
| A61M 11/02 | (2006.01) |
| A61M 31/00 | (2006.01) |
| A61B 90/00 | (2016.01) |

(52) U.S. Cl.
CPC .............. *A61K 6/002* (2013.01); *A61C 9/006* (2013.01); *A61K 6/10* (2013.01); *A61M 11/02* (2013.01); *A61M 31/005* (2013.01); *C09D 5/004* (2013.01); *C09D 5/021* (2013.01); *C09D 7/1216* (2013.01); *C09D 7/1233* (2013.01); *C09D 139/06* (2013.01); *A61B 2090/395* (2016.02)

(58) Field of Classification Search
CPC ........... C09D 5/004; A61K 6/002; C09K 3/30
See application file for complete search history.

(56) References Cited

U.S. PATENT DOCUMENTS
| | | |
|---|---|---|
| 3,431,208 A | 3/1969 | Bailey |
| 3,808,686 A | 5/1974 | Tauman et al. |
| 6,077,898 A | 6/2000 | Flores |

(Continued)

FOREIGN PATENT DOCUMENTS
| | | |
|---|---|---|
| WO | WO 98/48242 | 10/1998 |
| WO | WO 01/62209 | 8/2001 |

(Continued)

OTHER PUBLICATIONS

WO, PCT/EP2013/055642 ISR, dated Oct. 2, 2013.
WO, PCT/EP2013/055642 IPRP, dated Jul. 8, 2014.

*Primary Examiner* — Arrie L Reuther
(74) *Attorney, Agent, or Firm* — One LLP (57) ABSTRACT

Provided herein are compositions for applying a reference marker pattern or grid to the surface of an object to be imaged three-dimensionally. These compositions can be quick drying for ease of use. Methods of use of the compositions are also provided as well as devices and kits for the application of the compositions.

9 Claims, 5 Drawing Sheets

(56) References Cited

U.S. PATENT DOCUMENTS

| | | |
|---|---|---|
| 6,494,716 B1 | 12/2002 | Dorn et al. |
| 2002/0006600 A1 | 1/2002 | Cohen |
| 2011/0207074 A1* | 8/2011 | Hall-Holt ............... A61C 13/00 433/29 |
| 2011/0236587 A1 | 9/2011 | Clark et al. |
| 2011/0256070 A1 | 10/2011 | Martin et al. |
| 2012/0079961 A1 | 4/2012 | Shinozaki et al. |

FOREIGN PATENT DOCUMENTS

| | | |
|---|---|---|
| WO | WO 03/077839 | 9/2003 |
| WO | WO 2008/022850 | 2/2008 |
| WO | WO 2009/150596 | 12/2009 |
| WO | WO 2011/056574 | 5/2011 |
| WO | WO 2011/162965 | 12/2011 |
| WO | WO 2012/030357 | 3/2012 |
| WO | WO 2012/142110 | 10/2012 |

* cited by examiner

| Component | Working Examples | | | | | | | | | | | | | | |
|---|---|---|---|---|---|---|---|---|---|---|---|---|---|---|---|
| | 2 | 3 | 4 | 5 | 6 | 7 | 8 | 9 | 10 | 11 | 12 | 13 | 14 | 15 | 16 |
| Propellant | 94.25 | 94.25 | 92.50 | 95.70 (DME) | 92.50 (DME) | 98.12 | 94.50 | 96.25 | 94.25 | 88.50 | 92.50 | 87.76 | 92.50 | 88.50 | 88.50 |
| Intermediary Solvent | 3.60 | 4.00 | 3.20 | 0 | 3.20 | 0.80 | 1.60 | 1.60 | 3.20 | 8.00 | 3.20 | 7.22 | 3.20 | 7.60 | 8.00 |
| Polymeric Bonder | 0.40 | 0 | 0.80 | 0.80 | 0.80 | 0.20 | 0.40 | 0.40 | 0.80 | 0 | 0.80 | 1.52 | 0.80 | 0.40 | 0 |
| Black Particles | 0.75 | 0.75 | 1.50 | 1.50 | 1.50 | 0.38 | 1.50 | 0.75 | 0.75 | 1.50 | 1.50 | 1.50 | 2.10 | 0.88 | 0.88 |
| White Particles | 1.00 | 1.00 | 2.00 | 2.00 | 2.00 | 0.50 | 2.00 | 1.00 | 1.00 | 2.00 | 2.00 | 2.00 | 1.40 | 2.62 | 2.62 |

Composition Components (Percent by Weight) for Working Examples 2-16

*FIG. 3A*

| Component | Working Examples | | | | | | | | | | | | | |
|---|---|---|---|---|---|---|---|---|---|---|---|---|---|---|
| | 17 | 18 | 19 | 20 | 21 | 22 | 23 | 24 | 25 | 26 | 27 | 28 | 29 | 30 |
| Propellant | 88.50 | 88.50 | 88.50 | 88.50 | 88.50 | 88.50 | 88.50 | 88.50 | 88.50 | 88.50 | 88.50 | 88.50 | 88.50 | 92.30 |
| Intermediary Solvent | 7.60 | 8.00 | 7.60 | 8.00 | 7.60 | 8.00 | 8.00 | 7.20 | 8.00 | 7.20 | 8.00 | 7.20 | 8.00 | 4.00 |
| Polymeric Bonder | 0.40 | 0 | 0.40 | 0 | 0.40 | 0 | 0 | 0.80 | 0 | 0.80 | 0 | 0.80 | 0 | 0.20 (PVAL) |
| Black Particles | 3.00 | 3.00 | 2.62 | 2.62 | 2.10 | 2.10 | 1.32 | 0.55 | 0.55 | 0.95 | 0.95 | 1.50 | 1.50 | 2.33 |
| White Particles | 0.50 | 0.50 | 0.88 | 0.88 | 1.40 | 1.40 | 2.18 | 2.95 | 2.95 | 2.55 | 2.55 | 2.00 | 2.00 | 1.17 |

Composition Components (Percent by Weight) for Working Examples 17-30

CONTRAST PATTERN APPLICATION FOR THREE-DIMENSIONAL IMAGING

CROSS-REFERENCE TO RELATED APPLICATIONS

This application is a divisional application of U.S. patent application Ser. No. 14/638,915, filed Mar. 4, 2015, which is a continuation of U.S. patent application Ser. No. 13/424,200, filed Mar. 19, 2012, now U.S. Pat. No. 8,999,371, all of which applications are incorporated by reference herein in their entirety for all purposes.

FIELD

The subject matter described herein relates to devices for applying a contrast pattern on the surface of an object to be viewed and rendered by three-dimensional imaging system or platform, as well as the compositions carrying the contrast pattern and their methods of use.

BACKGROUND

A number of conventional platforms exist for the collection of two-dimensional image data of the surface of a subject (or object) and using that two-dimensional data to render (or otherwise represent) the object as a three dimensional computer model. The majority of these systems use electromagnetic radiation in the form of visible wavelengths to illuminate the surface of the object so that the reflections can then be received by an appropriate sensor or camera and placed into electrical format. These platforms have sophisticated hardware and software that process the received information in a fashion where the collected two-dimensional information can be used to render the three dimensional model.

A feature which has proved useful in accurately recognizing the surface of the object to be imaged is the application of reference markers to the object's surface. These reference markers are typically both reflective and opaque, and provide a high degree of contrast with the surroundings, enabling them to serve as reliable position indicators for the imaging optics.

An application for these platforms is the imaging of human teeth, such as for dentistry and orthodontics. A hand-held scanner is brought into proximity with the teeth, illuminates them, captures the reflected light, and sends that information to the processing segment, which can then use it to generate a three-dimensional model of part of a tooth, an entire tooth, or multiple teeth, etc. Crowns, orthodontics, molds, and the like can then be generated from the model. However, the human tooth is translucent and can vary in color, and its surface features are not always readily distinguishable by the imaging optics. It is therefore difficult to assess the surface features and an accurate location of the tooth exterior without the aid of the aforementioned reference markers.

The attempts to apply reference markers to the teeth described in prior publications are either insufficient or come with significant limitations. For instance, the composition disclosed in Intl. Publication No. WO 2009/150596 (Ernst) is in reality a bi-layer approach that requires application of a reference marker composition in two steps. A glue-type layer is applied first, and this is followed by the application of the reference markers in powdered form. The application of a composition bearing reference markers can be hindered if it does not dry fast enough. The patient can accidentally remove the composition with his or her tongue or saliva while it is applied or before the teeth have been fully imaged. Also, if the composition remains in liquid form long enough, the powder can run off or settle in an uneven manner across the tooth's surface (e.g., into crevices) resulting in reference markers being disproportionately allocated and hindering the creation of a dense, evenly distributed pattern. To combat this, Ernst uses a third, drying step in between application of the glue and the powder. A multiple step application process is time consuming and relatively more complex.

Intl. Publication No. WO 2011/162965 (Johnson) addresses the problem of slow drying compositions by applying a contrast composition that varies in viscosity based on changes in temperature. The composition is described as having low viscosity at ambient temperature and higher viscosity at body temperature, such that when the composition heats after application to the teeth it acts more like a gel and less like a liquid. However, a highly viscous composition tends to be thick when applied to the teeth. This can be problematic for the imaging system which must compensate for thickness of the composition to determine where the actual tooth surface lies. Also, because the composition does not fully dry, there remains a risk that it will rub or run off.

Intl. Publication No. WO 2011/056574 (Hall-Holt) recognizes the desirability of applying reference markers to teeth but does not describe the enabling specifics of a composition that can be used to apply those markers in practice. Hall-Holt suggests compositions that have a high viscosity, but does not disclose compositions that dry rapidly.

Intl. Publication No. WO 03/077839 (Butcher) discloses a composition that is predominantly alcohol and also uses a denture adhesive as a binding agent. Because of the high alcohol content (40%-94% by weight), this composition can potentially cause discomfort to a patient because of the thermal transfer that occurs during the evaporation of such a high alcohol content. This can be particularly troublesome with patients that have "cold-sensitive" teeth. Also, such a large alcohol content will typically take upwards of several minutes to dry.

New compositions and methods of their use are therefore needed to address these and other deficiencies in the current state of the art.

SUMMARY

Provided herein are compositions for application to the surface of an object to be imaged and modeled three-dimensionally, as well as methods for their use and devices (or kits) in which they can be included. These compositions can contain a multitude of reference markers that have a high contrast as compared to their surroundings and will be referred to as contrast pattern compositions herein. The reference markers are in the form of particles (or particulates) that can be disbursed in a dense and evenly distributed pattern across the surface of the object to be imaged. The compositions are suitable for numerous applications, including use on the teeth, where the compositions provide unique optical patterns against what can be a shiny and featureless surface. The composition can be applied from solution and can fully cover the underlying surface, substantially reducing or eliminating any undesirable surface reflections. The composition includes a bonding agent that bonds (or adheres) the particles to the surface relatively quickly enabling the composition to be "quick-drying" in certain embodiments.

Other compositions, systems, methods, features and advantages of the subject matter described herein will be or will become apparent to one with skill in the art upon examination of the following figures and detailed description. It is intended that all such additional compositions, systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

The contrast pattern compositions disclosed herein are typically manufactured and/or stored as a solution and subsequently applied as a spray. The composition preferably includes: (1) a particulate component that acts as an array or pattern of reference markers; (2) a bonding agent that bonds the particles to the surface of the object that is being imaged; and (3) a propellant for using of the composition as a spray. One or more intermediary solvents (co-solvent) can also be included to place the bonding agent in solution within the propellant. In other words, the bonding agent can be soluble within the intermediary solvent and the intermediary solvent can in turn be soluble within the propellant. In addition, the contrast pattern composition can include artificial or natural flavoring for use within or near the mouth.

The preferred application for the contrast pattern composition is in imaging of the teeth. Thus, a number of embodiments will be described herein with reference to that preferred application. However, it should be understood these embodiments are not for use solely in that context but have a wide range of applications, including the imaging of other parts of the human body (e.g., eye, nose, head, ear, or the like) or another living or non-living entity.

These embodiments will also be described with reference to a preferred method of application of the composition, i.e., as a spray, but it should be understood that the composition can be applied in a number of different ways, either in the form disclosed or in forms customized for other application techniques. These include, but are not limited to, application with a brush, airbrush, marker, paint pen-type applicator, mouthwash, by hand, and the like. These compositions can be applied as a powder, a liquid, and/or a gel. Preferably, the composition is initially applied in liquid form but rapidly dries into a solid (or semi-solid, gel, or sol).

Each component within the contrast pattern compositions is described herein both broadly as a class (or genus) and also as one or more subclasses (or sub-genuses or species). All combinations of classes and subclasses for one component are to be considered usable with all classes and subclasses of all other components unless noted otherwise. In other words, the various combinations of components that are within the scope of this disclosure should be interpreted broadly.

Figure 1:
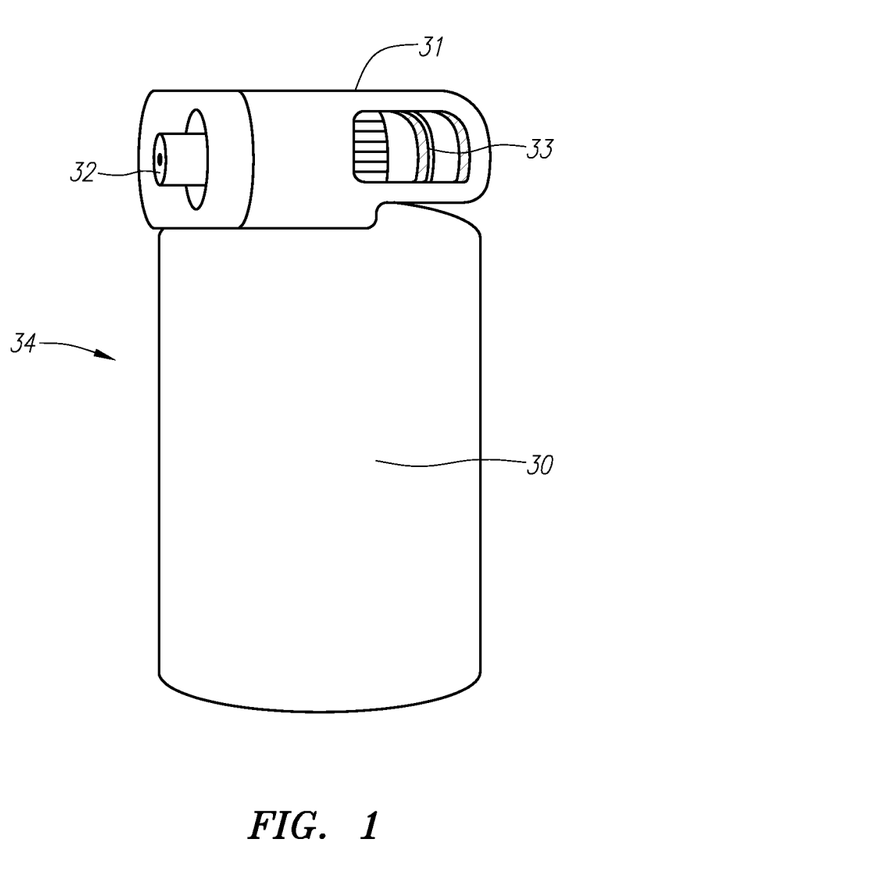
FIG. 1 is a perspective view of a device for applying a contrast pattern composition to a tooth.

FIG. 1 is a perspective view depicting an example embodiment of a spray device 34 for application of the contrast pattern composition. Spray device 34 includes a canister 30 for holding the contrast pattern composition under pressure. Spray device 34 includes a head 31 having a nozzle 32, which is in physical communication with the contents of the canister 30. The nozzle is preferably configured to atomize the contents of the canister as they are released. Head 31 also includes an actuator 33 for opening nozzle 32. Preferably, the contrast pattern composition includes a propellant that has a boiling point below room temperature, in combination with a product that contains the reference markers and a bonding agent. Opening of the nozzle allows the pressurized propellant to boil and spray the product outwards towards the object to be imaged.

Turning now to embodiments of the composition themselves, it should be understood that the type of particle used in the contrast pattern composition is very much dependent on the capabilities and requirements of the imaging platform with which it is to be used. Factors such as imager aperture size, sensor resolution, the number of channels, and the coding (e.g., by color, polarization, shape, etc.) of the channels, are examples of the considerations that are taken into account when selecting a particle. The size, shape, color and number of particles (percentage of the overall composition) are variables that can be adjusted to meet the desired specifications. The particles are preferably biocompatible and insoluble within the contrast spray composition. It is generally desirable to use the smallest particle size that is still distinguishable by the imaging system; however, particles less than one micron in size begin to risk absorption into the body in ways that may no longer justify referral to them as biocompatible. Preferably, the particles have a range of size of from about 1 micron to 50 microns, more preferably 5 microns to 20 microns, and more preferably 9 microns to 20 microns. Other sizes outside these ranges may also be used.

Generally, the thickness of the composition after application to the teeth should be minimized so that the particles being imaged most accurately represent the exterior surface of the tooth. The contrast pattern compositions, after application, preferably had a thickness in the range of 9-40 microns, more preferably 20-40 microns. Viewed from a different perspective, the contrast pattern compositions preferably have a thickness in the range of one to three (non-overlapping) particles in thickness, more preferably one to two particles in thickness. This refers to the long dimension of the particle in the case where the particles are significantly asymmetric.

Figure 2A:
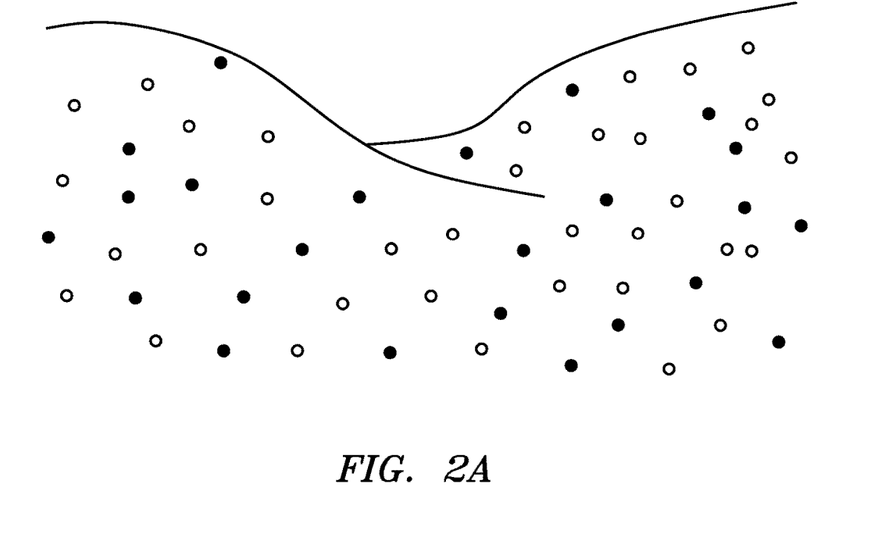
FIG. 2A is a side view showing spherical reference markers on the surface of a tooth.
Figure 2B:
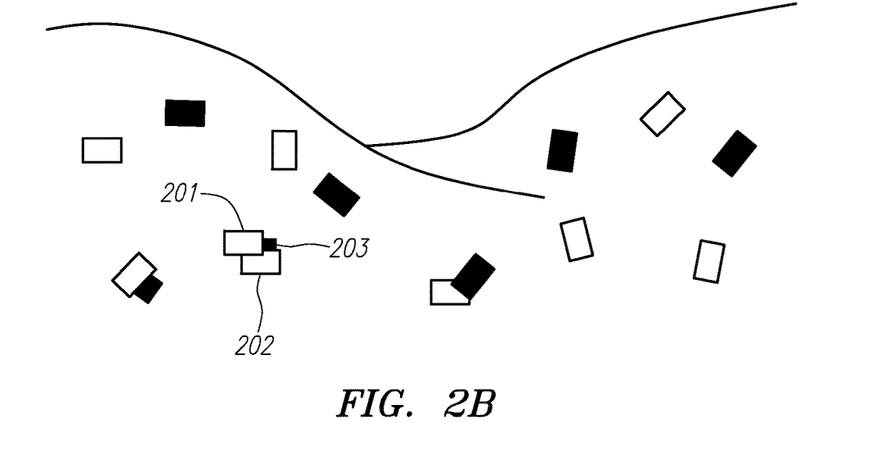
FIG. 2B is a side view showing flake-like reference markers on the surface of a tooth.

Particles that have a mostly planar shape, e.g., such as a flake or splinter, tend to stack up, one on top of the other, when applied to a surface. This can have the result of generating a greater than desired variability in particle size as imaged on the sensor. FIG. 2A depicts an example of evenly spaced spherical particles across a tooth surface, while FIG. 2B depicts an example of how particulate stacking can result in a higher variability in particle size. In FIG. 2B, two white flakes 201 and 202 are sitting above a black flake 203, where each are of equal size. Black flake 203 is partially obscured and appears to be only one-fourth the size of a white flake (e.g., 201). As a result, black flake 203 may be rendered too small to be accurately or reliably imaged by the sensor. In addition, the white flakes 201, 202 complement each other so as to appear larger than is needed for the sensor to distinguish them, which leads to inefficiencies in creating the densest possible pattern.

Spherical particles tend to space themselves apart and not stack up due to their fully rounded profile. Thus, spherical shapes and other similar shapes that do not significantly stack (referred to herein as "generally spherical" shapes) have proven most useful. These generally spherical shapes include, but are not limited to: balls of ovoid, elliptical, or irregular profiles; tall cylinders; tall prisms; rods; and polyhedrons without overtly planar shapes or box-like shapes (e.g., rounded or sharp edges, including pyramidal shapes, various pentahedrons, hexahedrons, and so forth). Those of skill in the art will readily recognize other shapes that will tend to avoid stacking.

The color of the particles is dependent on the needs of the application. The term "color" is used here broadly to refer to all the colors of the visible spectrum (black, white, red, orange, yellow, green, blue, indigo, violet, etc.) as well as all shades, tints, variations in grayscale, and the like. In one embodiment, the imaging system has two (or more) colored channels that are, e.g., red and blue (see the embodiments described with respect to FIG. 4). The particles are also divided into two colors, which provide a pattern having an inherent contrast with itself, making it more readily distinguishable when analyzed by the processing system. Black and white particles are one example of the color arrangement that can be used since each are distinguishable in both the red and blue channels.

Any color arrangement can be used so long as the one or more colors are distinguishable from each other and the surroundings. For instance, other color combinations that can be used in a blue and red channel system include green and white, green and black, violet and black, etc. If only a single blue channel is used, color combinations that are suitable include green and white, red and white, and blue and black (the blue appears white in a blue channel), etc. The particles themselves can also be given multiple colors, for instance, a spherical particle can have a black hemisphere and a white hemisphere. A number of other patterns or color combinations will be readily apparent to those of ordinary skill in the art. In addition to color variations, the particles can vary in polarization and appearance in the ultraviolet and infrared spectrums.

In terms of the material composition of the particles, it is generally desirable to use biocompatible materials that are inert and durable, such as ceramics, carbon variants, minerals, and certain polymers. Examples of suitable ceramics and minerals include, but are not limited to, titanium oxide, aluminum oxide, zinc oxide, zirconium dioxide, and talc, each of which generally are used for their white color. Examples of suitable polymers include, but are not limited to, polyethylene and polyethylene coated non-polymeric particles, polyester, and polyolefin. Polyethylene can be given any number of desired colors, including green, white, and black. Black particles can also be manufactured using carbon in a vitreous (e.g., glassy) or graphite form, or as a biocompatible ball coated with carbon nanotubes.

The particle is preferably inert since charged or polarized particles can be attracted or repelled by each other or by charges contained within the remainder of the composition. Such a phenomena can result in clumping or loss of the particles from the object's surface. The particles preferably have a high durability to avoid physically breaking down as fractured particles reduce the particle size and could render them undetectable by the sensor. Techniques to increase durability, such as sintering, are desirable where applicable. Black particles made from graphite tend to break down and thus are less preferred as compared to vitreous carbon. Also, particles made from conglomerates can tend to break down unless compensated for, such as through sintering.

The particles require an agent to fix them in position on the tooth, and the contrast pattern compositions include a bonding agent for that purpose. The bonding agent should have adhesive qualities, i.e., should be "sticky," and should be appropriate for human use. The bonding agents should also preferably be soluble in the propellant without the need of a slow drying intermediary solvent such as water. The bonding agent is also preferably water soluble to facilitate removal of the contrast pattern composition from the teeth and to allow better bonding when in the mouth.

The inventors have found that food grade polymers are a class of substances that can meet these requirements, either directly or indirectly. "Food grade" refers to those substances that have been qualified as food grade by the U.S. Food and Drug Administration (FDA). Polyvinylpyrrolidone (PVP) is an example of a polymeric bonding agent that is both food grade quality and relatively quick drying, making it particularly suitable for dental applications. The relative amount of PVP used is based upon the amount of particles in the composition; generally the minimum amount of PVP that will provide the desired amount of stickiness or adhesion to the teeth should be used.

PVP is not soluble in many propellants and therefore can require the use of an intermediary solvent to place it in solution. A suitable class of intermediary solvents that can be used are alcohols, including but not limited to denatured alcohol SBA 40, as they have the benefit of being relatively quick drying. The alcohol should not be highly toxic since the composition can be used within a patient's mouth. Other solvents for the bonding agent that are soluble within the chosen propellant can be used as well (e.g., water, glycerol, sorbitol, and xylitol).

Polyvinyl alcohol (PVAL) is another example of a suitable polymeric bonding agent. PVAL is not directly soluble in many propellants and can require an intermediary solvent such as alcohol or water. However, water typically adds to the dry time of the composition and this can require compensation. Other examples of bonding agents that can be used are solid polyvinyl acetate (widely used in chewing gums), starch, collagen, and other food polymers/thickeners.

The propellant can be any hydrofluorocarbon (HFC) (also referred to as hydrofluoroalkane (HFA)) in which the polymer or intermediary solvent is soluble. HFC examples include, but are not limited to: pentane; 2H, 3H decafluoropentane (HPFP); perfluoropentane (PFPt); propane; 1,1,1,2,3,3,3-heptafluoropropane (HFC 227); perfluoropropane (PFPr); ethane; 1,1,1,2-tetrafluoroethane (HFC 134a); 1,1,1,3,3,3-hexafluoropropane (HFC 236fa) and perfluoroethane (PFEt). Dimethyl ether (DME) can also be used (also referred to as methoxymethane). Chlorofluorocarbons (CFCs) can also be used but are heavily regulated in most markets, including the US. Preferably the propellant is of neutral polarity, non-flammable, and pharmaceutical grade. "Pharmaceutical grade" is intended to refer to the class of compounds that are approved for pharmaceutical use by the U.S. Food and Drug Administration. While pharmaceutical grade propellants are desirable, they are not required. Examples of pharmaceutical grade, non-flammable HFCs that can be used are HFC 134a (e.g., Zephex 134a), HFC 227ea (e.g., Zephex 227ea), and HFC 236fa (e.g., Dymel 236fa). Of these compounds, the inventors have found that HFC 227ea is most preferred.

In addition, the composition can be flavored and/or sweetened to make it more appealing to the patient. Those of ordinary skill in the art will recognize that a great number of flavorings (or combinations thereof) can be used. The flavoring preferably does not significantly interfere with the dry time are bonding characteristics of the composition.

The following working examples are provided to demonstrate a non-exhaustive list of compositions that the inventors found can function as a contrast pattern composition for three-dimensional imaging.

Working Example One

In this example, the composition is applied as a spray and uses HFC 227ea as the propellant. Table 1 shows the components in the percent by which they make up the composition.

TABLE 1

| Substance | Percent (by weight) |
| --- | --- |
| 1,1,1,2,3,3,3-heptafluoropropane (Zephex 227ea) | 92.285 |
| denatured alcohol (SDA) 40B | 3.600 |
| titanium dioxide (9-20 microns) | 2.000 |
| glassy carbon (10-20 microns) | 1.500 |
| polyvinylpyrrolidone (PVP) | 0.400 |
| spearmint flavor | 0.200 |
| sodium saccharin sweetener | 0.015 |

Titanium dioxide spherical particles were used as the white reference markers while glassy (vitreous) carbon spherical particles were used as the black reference markers. The bonding agent used to bond these particles to the teeth is PVP (also referred to as kollidon 30). PVP is not typically soluble in Zephex 227ea so an intermediary solvent (co-solvent) is used, which is denatured alcohol (SBA) 40B in this example. PVP is advantageous because it is soluble in alcohol without needing water. It has been found that the minimum amount of PVP that provides adequate bonding of the particles to the teeth, in this example, is a ratio of about 1:8.75 as compared to the amount of white and black particles. Thus, in applications that require relatively more or less particles for imaging, the amount of PVP can be adjusted while maintaining the same or similar ratio (e.g., between about 1:8 and 1:10). A broader ratio can be used, however, such as between about 1:6 and 1:12 (PVP:particles). An alcohol content of about 9:1 as compared to the PVP content is used to place the PVP in solution. A relatively small amount of spearmint flavoring and saccharin for sweetness are also included.

This composition, while kept in solution within the spray canister, dries very rapidly upon exiting the canister and coming to rest on the teeth. This "quick dry" composition is beneficial in that the composition has little time to be wiped away when coming into contact with the teeth and also very little time for the particles to group or drain off of the teeth in a way that would interfere with creating an evenly-distributed and dense reference grid. This also provides immediate feedback for the administering user as to the sufficiency of coverage of the teeth. The use of PVP results in a firm bond that is not easily wiped away with the tongue, cheeks or lips and, therefore, will remain in place throughout the imaging procedure. However, because PVP is water soluble, it can be readily removed by use of a water stream such as a dentist's water jet. It can also be removed by a mouthwash or other removal applicator, such as a brush.

Figure 3A:
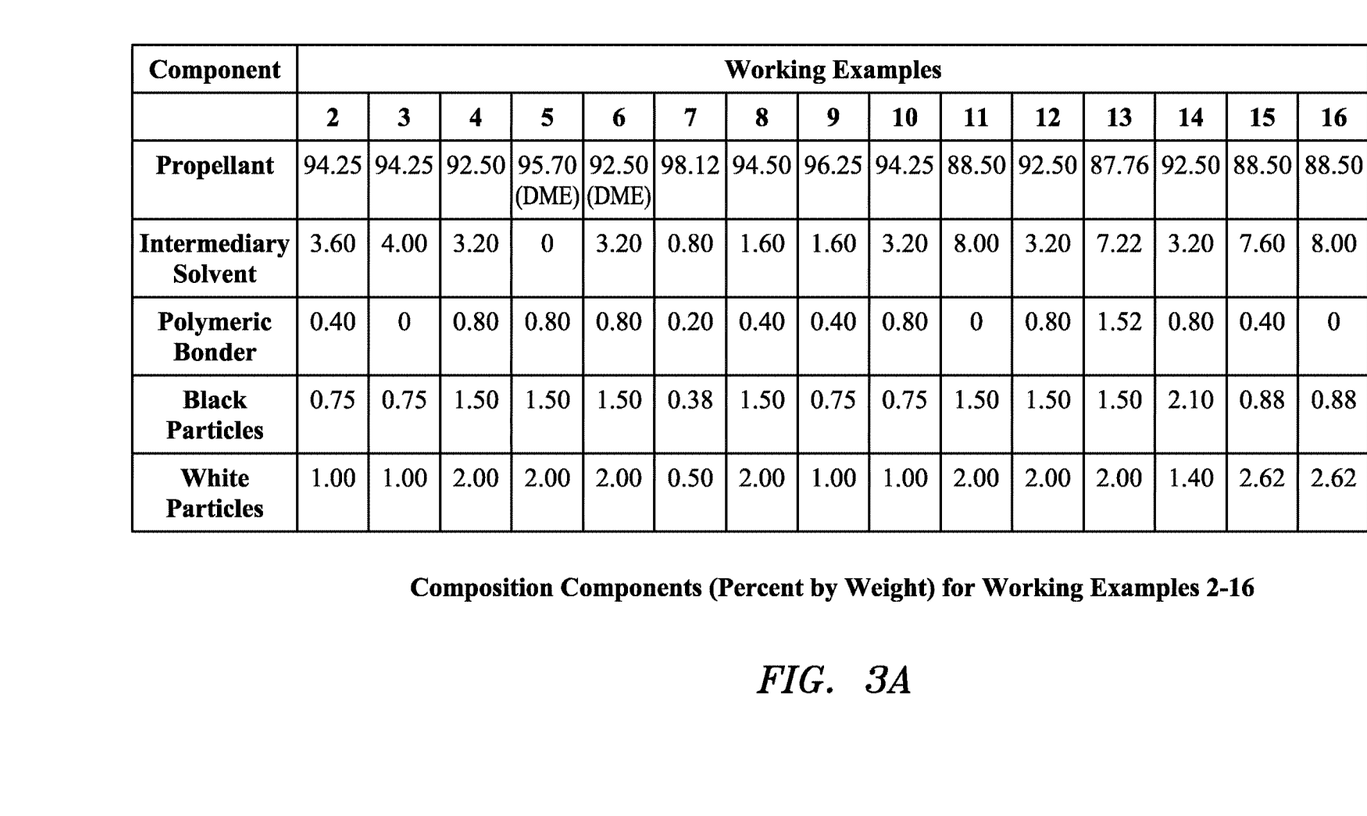
FIG. 3A is a table listing the percent by weight of the components of the contrast pattern composition for working examples two through sixteen.
Figure 3B:
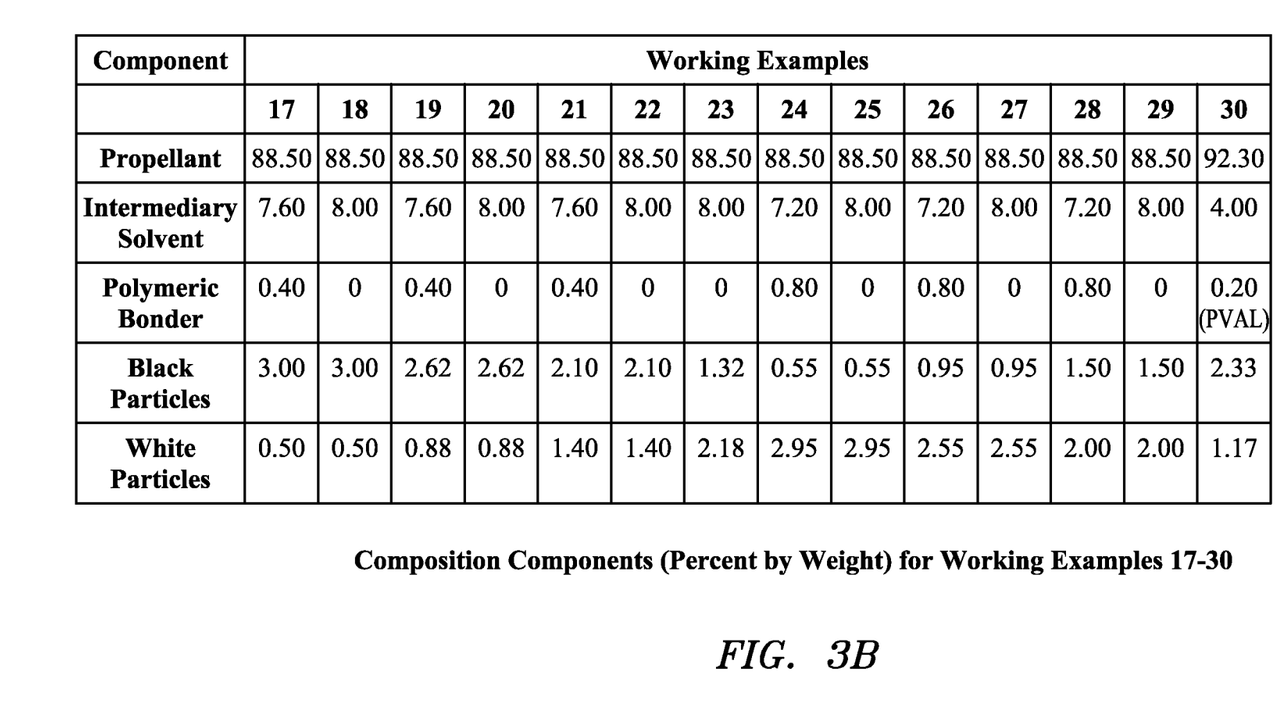
FIG. 3B is a table listing the percent by weight of the components of the contrast pattern composition for working examples seventeen through thirty.

An additional twenty-nine working examples are set forth in FIG. 3A (examples 2-16) and FIG. 3B (examples 17-30). In these examples, percent compositions for each of various components (propellant, intermediary solvent, polymeric bonder, black particles, and white particles) to arrive at functioning compositions with varying degrees of performance. (No flavoring was included in these examples.) Unless otherwise stated in the tables of FIGS. 3A-B, the propellant in each example is HFC 227ea, the intermediary solvent is denatured alcohol SBA 40, the polymeric binder is PVP, the black particles are glassy carbon, and the white particles are titanium dioxide. Some working examples did not have a polymeric bonder (examples 3, 11, 16, 18, 20, 22-23, 25, 27, and 29). Also, working example 5 did not have an intermediary solvent. The diameters of the white particles ranged from nine to twenty microns, except that the diameters for examples 17-22 ranged from nine to thirty-two microns, the diameters for example 23 were less than five microns, and the diameters for examples 24-29 ranged from one to ten microns. The diameters of the black particles ranged from ten to twenty microns for each example.

Methods of use of the contrast pattern compositions are also provided herein. In one example embodiment, the contrast pattern composition is applied to the teeth from a spray canister. The spray is applied to all surfaces of all teeth to be imaged. The composition exists in the canister in an un-dried or non-solid form (e.g., as a gas or liquid solution) carrying the suspended particle reference markers, but the propellant and other components begin to dry immediately upon exiting the spray canister assembly (e.g., the nozzle). The contrast pattern composition is therefore quick drying and dries (or sets) in the range of immediately after exiting the nozzle to about ten seconds after initial contact with the tooth under ambient conditions (conditions of the human mouth in an external environment at room temperature).

In another embodiment, the contrast pattern composition dries (or sets) in the range of immediately after exiting the nozzle to about seven seconds after initial contact with the tooth under ambient conditions. In yet another embodiment, the contrast pattern composition dries (or sets) in the range of immediately after exiting the nozzle to about five seconds after initial contact with the tooth under ambient conditions. In still yet another embodiment, the contrast pattern composition dries (or sets) in the range of immediately after exiting the nozzle to about one second after initial contact with the tooth under ambient conditions.

The contrast pattern composition dries (or sets) without the application of heat or gas (e.g., air) from an external heating source, blowing apparatus, or other device (i.e., without the application of heat or gas from a source other than the body of the patient and the ambient surroundings). For instance, no affirmative "drying step" is required to cause the composition to dry. Also, no significant "waiting period" (on the order of 10 seconds or more) is required to allow the composition to dry (or set) on the teeth. Use of the term "dry" refers to the state where the particles are set in position and are no longer moveable, which corresponds to the composition being in a solid or substantially solid state.

The method can also include the removal of the dried (or set) composition with the use of a water spray apparatus (e.g., a dental water jet).

These contrast pattern compositions can be customized or varied to work with any number of three-dimensional imaging systems. Embodiments of a typical imaging system with which the contrast pattern composition is particularly suited are now described. It should be noted that this typical imaging system is an example only and is in no way intended to limit the types of imaging systems or techniques of imaging with which the composition can be used.

Figure 4:
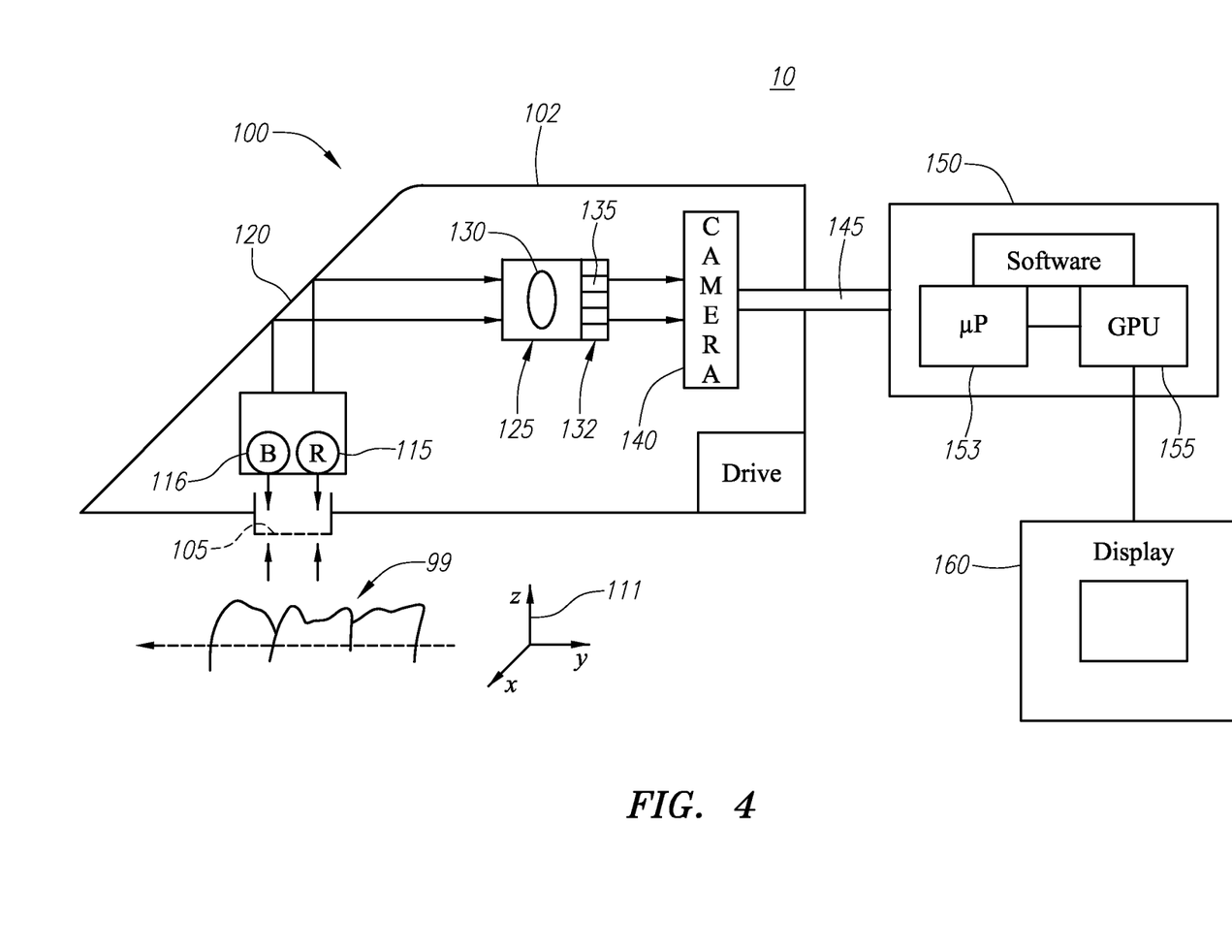
FIG. 4 is a block diagram depicting an example embodiment of a three-dimensional optical imaging system.

FIG. 4 depicts a block diagram of an example embodiment of the hardware of a three-dimensional imaging system 10. System 10 can be provided in combination with the contrast pattern compositions and applicator device (e.g., spray device 34) in the form of a kit.

A handheld scanner 100 is provided for use in imaging an object 99. Scanner 100 has an outer housing 102 that holds a number of optical and electrical items. The scanner can include any type of camera 140 or any other device that receives optical information and converts it into electrical information. For example, this may be a charge coupled device (CCD) sensor, complementary metal oxide semiconductor (CMOS) image sensor, or any other kind of photo sensor that converts light photons into electrical signals. Camera 140 produces output information that typically contains two-dimensional data from which three-dimensional information of object 99 can be determined. The two-dimensional information may be referred to as x and y coordinates, defined as coordinates that are perpendicular to a z axis direction 111 between scanner 100 and object 99. The three-dimensional information may include z axis coordinates that are orthogonal to the x and y axes and are indicative of the distance between camera 140 and object 99.

The image information may be stored as coordinates or may be stored in any other form, such as a three-dimensional point cloud, a three-dimensional mesh, or any other form that can represent two-dimensional and/or three-dimensional information.

A window 105 is formed in the portion of scanner 100 that allows the light from object 99 to enter. In this embodiment, object 99 is a set of human teeth and system 10 is used to render a three-dimensional image of the teeth. However, object 99 may be any object, collection of objects, portion of an object, or other entity of which it is desired to generate a three-dimensional image. For example, in the dental imaging environment, object 99 may be a tooth, a portion of a tooth, a quadrant of teeth, or the full collection of teeth of a patient. Such information is useful in numerous applications, including the creation of a virtual dental impression for use in dentistry procedures. In other embodiments, object 99 may be some other entity, e.g., a part of the human body (eye, nose, head, ear or the like) or another living entity, or a nonliving entity.

An illuminator comprising different color light elements 115, 116 applies light onto the teeth 99. The image of the illuminated object is received through window 105. A corner mirror 120 reflects the received electromagnetic radiation to optics 125. In other embodiments, the system can operate without a corner mirror.

Optics 125 may include a lens 130 and a mask 132 with multiple apertures 135. Apertures 135 may be color coded, i.e., one aperture may pass only or substantially only a single color and the other may pass only or substantially only light of another color. For example, in a two aperture system, one of the apertures 135 can be blue and the other red. Light elements 115, 116 may provide colors that match the colors of the apertures (indicated as B and R in the figure). This produces two different channels of information, one through each of the two apertures.

The light that passes through apertures 135 is provided to camera 140 (e.g., a sensor) that produces electronic outputs indicative of the intensity, color and location of the received light. Camera 140 is connected to a computing device 150 that includes software for driving sensor 140 and analyzing the received information. Computing device 150 can be a general purpose processor with a microprocessor 153 operating according to a stored program as described in the co-pending application entitled Three-Dimensional Imaging System, Intl. Application No. PCT/US2010/057532, which is hereby incorporated by reference in its entirety for all purposes. Computing device 150 may also, or alternatively, include a graphics processing unit (GPU) 155, e.g., in a video card that drives a display 160. GPU 155 can be an ATI or an Nvidia video card or the like. Computing device 150 may alternatively include a field programmable memory (e.g., a Gateway) or any custom hardware or custom logic.

In one embodiment the portable handheld scanner 100 can be moved while obtaining information about the scanner area as the scanner moves. At each of a plurality of different times, new information about object 99 is obtained along with new information about the camera's position. This allows the overall object 99 to be rendered in full even though the electromagnetic radiation received through window 105 typically represents only a small fraction of the surface of object 99.

Sensor 140 may be any standard sensor or camera (e.g., one-third inch COS megapixels CMOS digital image sensor as produced by Micron Technology, Inc.), including those having a color filter array that is already with the photosensors themselves to separate the colors. The filters on the color filter array portion of the camera 140 separate between the color rays (here red and blue channels) to obtain the information and distinguish between the color rays passed by the color filters on apertures 135. The information from each color filtered aperture is picked up only by the appropriate filter portion of the camera 140.

The color filter array can be a Bayer filter such as described in U.S. Pat. No. 3,971,065 or alternatively and be a different kind of color filter such as the CYGM filter and the RGBE filter or a custom filter array (e.g., if there are two apertures which are coded as blue and red, the filter array would have alternating filters of blue and red). A camera incorporating a custom two-color filter would have the advantage of using all the available sensor area in connection with the two-color, two-aperture system.

It should be noted that various embodiments are described herein with reference to one or more numerical values. These numerical value(s) are intended as examples only and in no way should be construed as limiting the subject matter recited in any claim, absent express recitation of a numerical value in that claim.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A composition for use in coating an object to be imaged with a three-dimensional imaging system, comprising:
   a plurality of titanium dioxide particles;
   a plurality of vitreous carbon particles;
   a polymeric bonder selected from the group consisting of polyvinylpyrrolidone and polyvinyl alcohol;
   a propellant selected from the group consisting of 1,1,1,2-tetrafluoroethane, 1,1,1,2,3,3,3-heptafluoropropane, and 1,1,1,3,3,3-hexafluoropropane; and
   denatured alcohol.

2. The composition of claim 1, wherein the propellant is 1,1,1,2,3,3,3-heptafluoropropane.

3. The composition of claim 2, wherein the polymeric bonder is polyvinylpyrrolidone.

4. The composition of claim 1, wherein the polymeric bonder is polyvinylpyrrolidone.

5. The composition of claim 4, wherein the propellant is 1,1,1,2,3,3,3-heptafluoropropane.

6. The composition of claim 1, wherein the denatured alcohol is denatured alcohol SDA 40B.

7. The composition of claim 1, further comprising artificial flavor.

8. The composition of claim 1, wherein the ratio of the plurality of titanium dioxide particles and the plurality of vitreous carbon particles to the polymeric bonder is between twelve-to-one and six-to-one.

9. The composition of claim 1, wherein the ratio of the plurality of titanium dioxide particles and the plurality of vitreous carbon particles to the polymeric bonder is between nine-to-one and eight-to-one.

* * * * *